United States Patent [19]

Kaiser

[11] 4,226,770

[45] Oct. 7, 1980

[54] SYNTHESIS OF STEROIDS

[76] Inventor: Emil T. Kaiser, 5634 S. Woodlawn Ave., Chicago, Ill. 60637

[21] Appl. No.: 14,695

[22] Filed: Feb. 23, 1979

Related U.S. Application Data

[63] Continuation of Ser. No. 876,753, Feb. 10, 1978, Pat. No. 4,163,744.

[51] Int. Cl.³ .............................................. C07J 21/00
[52] U.S. Cl. ...................... 260/239.55 C; 260/397.2; 260/397.1
[58] Field of Search .............................. 260/239.55 C; /Steroids MS File

[56] References Cited

U.S. PATENT DOCUMENTS

| | | | |
|---|---|---|---|
| 4,134,904 | 1/1979 | Kaiser | 260/397.2 |
| 4,163,744 | 8/1979 | Kaiser | 260/239.55 C |

*Primary Examiner*—Elbert L. Roberts
*Attorney, Agent, or Firm*—Carl C. Batz

[57] ABSTRACT

The synthesis of 1α,25-dihydroxycholesterol, 1α,25-dihydroxy-7-dehydrocholesterol and 1α,25-dihydroxycholecalciferol and other sterol derivatives from bile acids. Also the synthesis of 3,6-diketo steroids useful in the production of 1α,25-dihydroxycholesterol and other sterols which are biologically active or can be converted to biologically active sterols. The invention involves the sterols so produced and the processes by which they are prepared.

18 Claims, No Drawings

SYNTHESIS OF STEROIDS

This is a continuation of application Ser. No. 876,753 filed Feb. 10, 1978 now U.S. Pat. No. 4,163,744.

This invention relates to the synthesis of steroids and more particularly to the synthesis of 1α,25-dihydroxycholesterol and to precursor steroids and derivatives thereof.

BACKGROUND OF THE INVENTION

Vitamin $D_3$ (cholecalciferol) has been known for many years. It may be prepared from cholesterol by the introduction of an additional bond into the cholesterol molecule to produce 7-dehydrocholesterol and subjecting the 7-dehydrocholesterol to ultraviolet radiation. It was at one time thought to be biologically active in the regulation of intestinal calcium transport and the mobilization of calcium from bone. More recently it has been discovered that to be biologically active cholecalciferol has to be hydroxylated in the body to 25-hydroxycholecalciferol or hydroxylated derivatives thereof, particularly 1α,25-dihydroxycholecalciferol. It would, therefore, be important to prepare and administer such hydroxylated derivatives, particularly 1α,25-dihydroxycholecalciferol, instead of Vitamin $D_3$.

The synthesis of 25-hydroxycholesterol, a precursor of 25-hydroxycholecalciferol, by practical methods is set forth in my co-pending patent applications Ser. No. 816,478 filed July 18, 1977 now U.S. Pat. No. 4,183,852 and Ser. No. 829,009 filed Aug. 30, 1977 now U.S. Pat. No. 4,134,904. It would now be important indeed to discover practical and effective methods for the synthesis of 1α,25-dihydroxycalciferol and its derivative 1α,25-dihydroxycholecalciferol.

Earlier publications disclosed the synthesis of 1α,25-dihydroxycholesterol from cholesterol and stigmasterol. In these syntheses intermediates for the 1α-hydroxylation were needed which had a 6-ketone group in the steroid nucleus in addition to a 3-keto group, which could be obtained by the oxidation of the 3-hydroxyl function. Since cholesterol and stigmasterol have a 5,6-double bond, the required 6-keto group had to be introduced synthetically in several steps.

The first synthesis of 1α,25-dihydroxycholesterol started from an oxidation product of cholesterol (E. J. Semmler, M. F. Holic, H. K. Schnoes and H. S. DeLuca, Tetrahedron Letters, 4147 (1972)). In this synthesis, the 1α-hydroxyl group was introduced into the steroid nucleus through an intermediate containing a 6-keto group. Since cholesterol has a 5,6-double bond, the 6-keto group had to be introduced synthetically. This required three operations, nitration, reduction and acid hydrolysis, to produce the 6-keto intermediate. In another synthesis, which started with stigmasterol (T. A. Narwid, J. F. Blount, J. A. Iacobelli and M. R. Uskokovic, Helvetica Chim. Acta, 57, 781 (1974)), treatment of 25-hydroxycholesterol acetate with diborane followed by the addition of hydrogen peroxide, yielded a mixture of which the main component was a triol. This triol was then oxidized to the 25-hydroxy-3,6-dione, from which the 1α,25-dihydroxycholesterol was synthesized.

In the procedures above described the introduction of the 6-keto group occurred in advanced stages of the synthesis, where even small losses of material add significantly to the cost of producing the final product.

SUMMARY

I have discovered that by starting with hyodeoxycholic acid, an acid which may be derived from hog bile, or derivatives thereof, it is possible to synthesize a number of 3,6-diketo steroids which are useful for the introduction of the 1α-hydroxyl group. These 3,6-diketo steroids are useful particularly in the synthesis of 25-hydroxycholesterol, 25-hydroxy-7-dehydrocholesterol, 25-hydroxycholecalciferol, 1α,25-dihydroxycholesterol, 1α,25-dihydroxy-7-dehydrocholesterol and 1α,25-dihydroxycholecalciferol.

According to the present invention, hyodeoxycholic acid (3α,6α-dihydroxycholanic acid), or an ester thereof, is oxidized to the 3,6-diketo-5α-cholanic acid, or an ester thereof, which is a starting material for the synthesis of my novel 3,6-diketo steroids. From the beginning of this synthesis the 6-keto group is present, thus eliminating any need for it to be introduced into the steroid nucleus by several steps and in advanced stages of the process.

DISCLOSURE OF THE INVENTION

My improved synthesis may start with 3,6-diketo-5α-cholanic acid, or esters thereof, obtained by the oxidation of hyodeoxycholic acid or esters thereof (T. F. Gallagher and J. R. Xenox, J. Biol. Chem., 165, 365 (1946)).

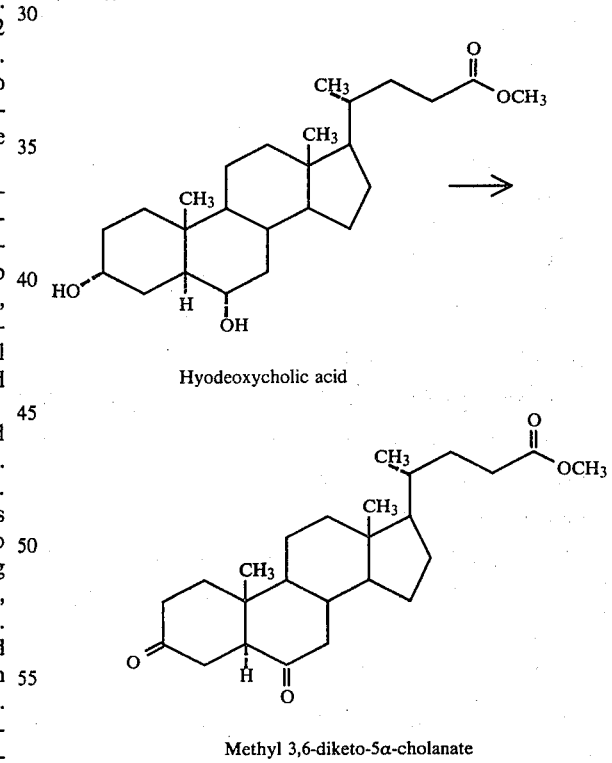

Hyodeoxycholic acid

Methyl 3,6-diketo-5α-cholanate

Instead of methyl ester, other lower alkyl esters such as the ethyl, propyl or butyl esters of hyodeoxycholic acid can be used ("alkyl" is used to include the saturated as well as the unsaturated form of the group). The choice of the ester group may be guided mainly by economic considerations and solubility properties of the esters. I prefer the methyl ester, since it can be isolated directly from esterified crude hog bile acid as a toluene or benzene complex.

The starting material of my synthesis my be written as:

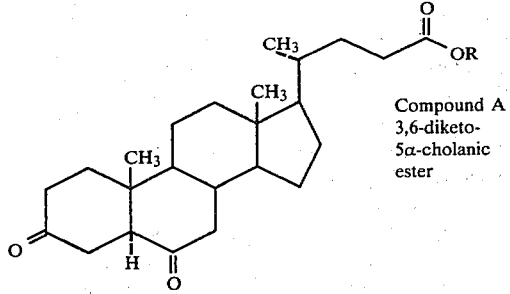

Compound A
3,6-diketo-5α-cholanic ester where R is a lower alkyl group, or I may start with the methyl ester as it is obtained from esterified hog bile acids. In either case, the keto ester may be heated with ethylene glycol and a sulfonic acid such as p-toluenesulfonic acid, as a catalyst, to prepare methyl 3,6-dioxo-5α-cholanate diethylene ketal which has the structure:

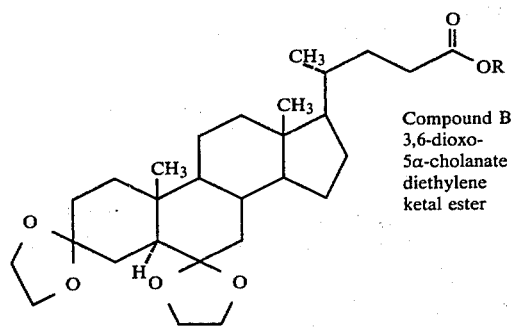

Compound B
3,6-dioxo-5α-cholanate diethylene ketal ester where R is a lower alkyl group.

By forming ketal derivatives of 3- and 6-keto groups, the steroid nucleus is protected against subsequent reactions involving alkaline reducing agents preliminary to the extension of the side-chain by one carbon. Such reducing agents may be sodium, potassium or lithium complexes of aluminum hydride, which reduce the carboxylic ester groups to primary alcohols.

Compound B may be treated with such a reducing agent to reduce the 24-carboxylic ester group to a 24-hydroxyl group. The complexes of sodium, potassium or lithium with aluminum hydride do not affect the protected nucleus of Compound B. The reduction, in one of its forms, can be carried out in benzene solution with sodium bis(2-methoxyethoxy)aluminum hydride (Vitride) by refluxing for a period sufficient to complete the reaction, which may be, for example, one to two hours. The compound so obtained has the structure:

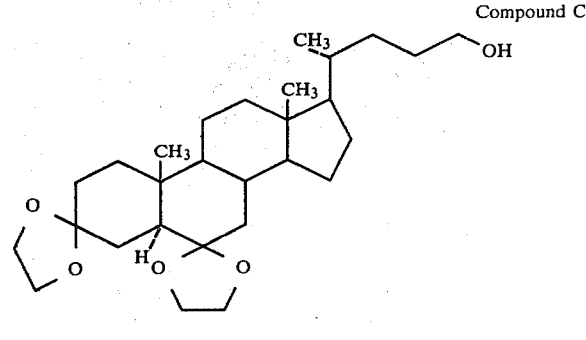

Compound C

Compound C may be mixed with an aromatic sulfonyl halide, such as p-toluenesulfonyl halide in pyridine solution, and allowed to react to replace the hydroxyl group with an aromatic sulfonyl ester function, such as the p-toluenesulfonyl ester group, to obtain Compound D which may be written as:

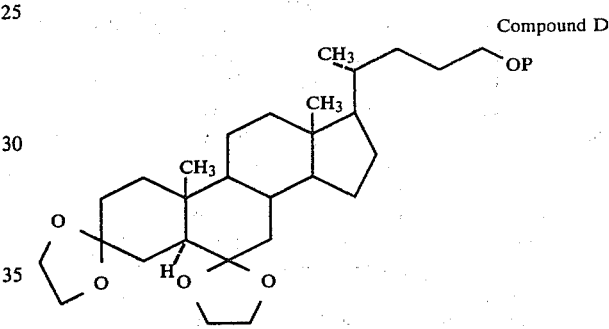

Compound D in which P is an aliphatic or aromatic sulfonyl group.

Optionally, and in place of the aromatic sulfonyl ester function, Compound C may be allowed to react with an alkyl sulfonyl halide, such as methane sulfonyl halide, to form an aliphatic sulfonyl ester. This may be accomplished by mixing Compound C in pyridine solution with an alkyl sulfonyl halide and allowing the reaction to proceed to replace the hydroxyl group with an aliphatic sulfonic acid ester function, such as the methyl sulfonyl group.

Compound D may be treated with a metallic cyanide, preferably potassium cyanide, but other metallic cyanides, such as sodium cyanide, lithium cyanide or silver cyanide may also be used to replace the side-chain sulfonyl ester with a CN function. The side-chain now has been extended by one carbon, and a 25-carbon structure obtained with the carbon of CN being carbon 25.

In one of its forms the reaction between Compound D and potassium cyanide can be carried out by heating in dimethylformamide (DMF) for a period until the reaction is complete, for example, for about 24 hours. The resulting compound is the 3,6-dioxo-25-cyano-5α-cholane diethylene ketal which has the structure:

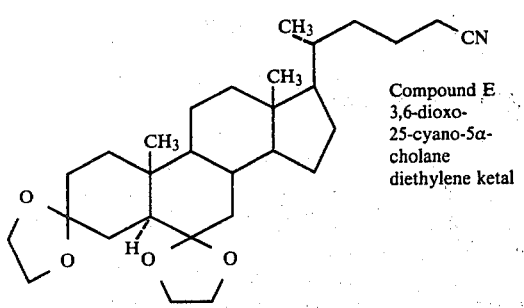

Compound E
3,6-dioxo-
25-cyano-5α-
cholane
diethylene ketal

The cyano group of Compound E may be transformed into a carboxyl group by refluxing with potassium hydroxide in an aqueous alcohol solution. On acidification, the free acid 3,6-dioxo-25-carboxy-5α-cholane diethylene ketal is obtained having the structure:

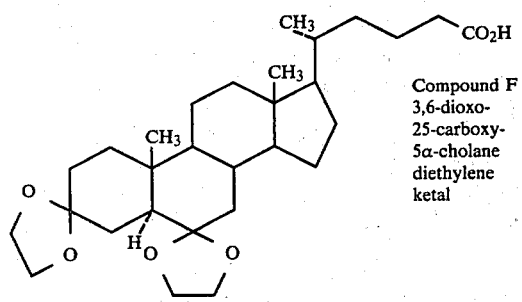

Compound F
3,6-dioxo-
25-carboxy-
5α-cholane
diethylene
ketal

The carboxyl group of Compound F may then be esterified. In one of its forms, Compound F is treated with methyl iodide in a solvent such as hexamethyl phosphoric triamide, to which an aqueous sodium or potassium hydroxide solution is added. In place of methyl iodide, other alkyl halides, for example, ethyl bromide, can be used to obtain the 3,5-dioxo-25-carboalkoxy-5α-cholane diethylene ketal, having the structure:

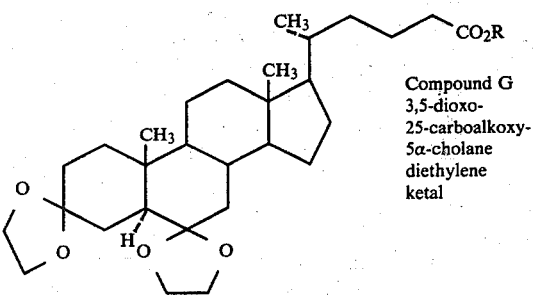

Compound G
3,5-dioxo-
25-carboalkoxy-
5α-cholane
diethylene
ketal where R is alkyl, such as methyl, ethyl or butyl.

Compound G may be mixed with a methyl Grignard reagent, preferably methyl magnesium bromide, in a tetrahydrofuran solution, and allowed to react to obtain the 25-hydroxycholestane-3,6-dione diethylene ketal, having the structure:

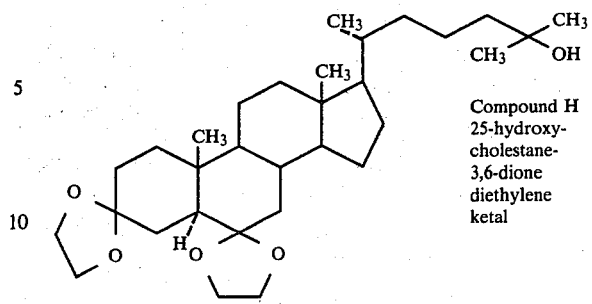

Compound H
25-hydroxy-
cholestane-
3,6-dione
diethylene
ketal

Compound H may be refluxed in an alcohol solution containing aqueous sulfuric acid until the ketal protection is removed, for example, for a period of one or two hours, to obtain the 25-hydroxycholestane-3,6-dione having the structure:

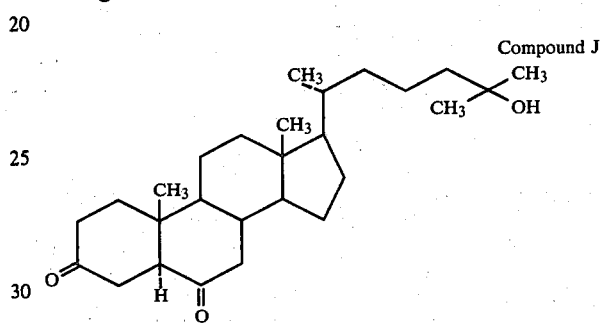

Compound J

Compound J can be transformed by methods known in the art to 1α,25-dihydroxycholesterol.

Such methods are described in Helvetica Chimica Acta, 57, 781 (1974) by T. A. Narwid, J. F. Blount, J. A. Iacobelli and M. R. Uskokovic, and also in U.S. Pat. No. 3,887,505.

The synthesis of Compound J can be carried out in overall yields which may be of the order of 50 to 55% when starting with methyl hyodeoxycholate. The economic advantages of this process are due at least in part to the hyodeoxycholic acid starting material since this material is easily obtained from hog bile which is regarded at this time as a waste material. The synthesis can be carried out easily with equipment generally available in chemical manufacturing plants with the use of reasonably priced commercially available chemicals.

To illustrate more specifically how the reactions may be practiced in my improved synthesis, the following specific examples are set forth.

EXAMPLE 1

Conversion of Methyl Hyodeoxycholate to Methyl 3,6-dioxocholanate (Compound A)

To a stirred solution of 138.10 g (0.3397 mole) of methyl hyodeoxycholate in 3.5 l of reagent grade acetone maintained at 10°–15° C., 215 ml of a solution of 267.2 g of chromium trioxide in a mixture composed of 230 ml sulfuric acid and 400 ml water, diluted to one liter, was added dropwise over a period of 1 hour. After an additional hour of stirring at 10° C., the reaction mixture was filtered to remove chromium salts, and the orange colored filtrate was filtered through activiated charcoal to afford a clear, nearly colorless solution which upon concentration to dryness gave 119.60 g (87%) of A as a white powder, m.p. 135°–137° C. Recrystallization of this material from acetone-water gave an analytical sample of the methyl 3,6-dioxo cholanate (A) as a white crystalline solid, m.p. 140°–141° C.; ir (CHCl$_3$) 2950, 2875, 1720 cm$^{-1}$; nmr (CDCl$_3$) δ 3.65 (3H, S, —OCH$_3$), 2.15–2.52 (9H, m, adjacent to carbonyl), 0.95 (3H, S, C-19—CH$_3$) 0.70 (3H, S, C-18—CH$_3$): mass spectrum (m/e) 402 (M+), 387.

Anal. Calc'd for C$_{25}$H$_{38}$O: C, 74.59; H, 9.51; O, 15.90. FOUND: C, 74.54; H, 9.28; O, 15.76.

EXAMPLE 2

Preparation of Methyl 3,6-dioxo-5α-cholanate diethylene ketal (Compound B)

A stirred solution of 30.80 g (0.076 mole) of A, 73.70 g (1.1875 mole) of ethylene glycol, and 0.6 g of p-toluenesulfonic acid in 803 ml of benzene in a 2 l single necked flask fitted with a Dean-Stark trap was heated at reflux for 65 hours. After cooling to room temperature, the benzene solution was washed with 1×200 ml of a saturated solution of sodium bicarbonate, 2×200 ml of water, dried (MgSO$_4$), filtered through activated charcoal and the benzene removed under reduced pressure to afford 38.00 g (100%) of a viscous, nearly colorless liquid. A small amount of this material was dissolved in diethyl ether and again filtered through activated charcoal. The filtrate was concentrated to dryness to afford, after vacuum drying, the diethylene ketal B as a white crystalline solid, m.p. 92°–97° C. Recrystallization of this sample from n-heptane gave the ketal as a white crystalline solid, m.p. 95°–98° C.; ir (CHCl$_3$) 2950, 2880, 1730, and 1100 cm$^{-1}$; nmr (CDCl$_3$) δ 3.77–4.05 (8H, m, —OCH$_2$CH$_2$O—), 3.66 (3H, S, —OCH$_3$), 1.00 (3H, S, C-19 —CH$_3$), 0.66 (3H, S, C-18 —CH$_3$); mass spectrum (m/e) 490 (M+), 446, 418, 293.

Anal. Calc'd for C$_{29}$H$_{46}$O$_6$: C, 70.99; H, 9.45; O, 19.56. Found: C, 70.83; H, 9.42; O, 19.58.

EXAMPLE 3

Preparation of 3,6-dioxo-24-hydroxy-5α-cholane diethylene ketal (Compound C)

To a refluxing solution of 44 ml (0.158 mole) of vitride reagent [sodium bis(2-methoxyethyl)-aluminum hydride] in 130 ml of dry benzene under an argon atmosphere was added dropwise a solution of 35.30 g (0.072 mole) of B in 200 ml of benzene over a period of 1 hour. After an additional hour of reflux the reaction mixture was allowed to cool to room temperature and then added via a separatory funnel to 120 ml of 20% aqueous sodium hydroxide over a period of 1 hour with cooling. The layers were separated and the aqueous layer washed with 3×25 ml of benzene. Combined benzene extracts were washed with 50 ml of water, dried (Na$_2$SO$_4$), and filtered to afford a clear orange solution. This solution was heated with activated charcoal for 10 minutes and filtered to afford a nearly colorless solution. Concentration under reduced pressure gave 32.80 g (98%) of a nearly colorless viscous liquid. This material, upon drying in a vacuum oven, became a white solid, m.p. 60°–65° C. When this sample was dissolved in 135 ml of acetone and then treated with 500 ml of water an oil formed. This solution was decanted and upon drying the oil became a white solid, C, m.p. 73°–76° C., ir (CHCl$_3$) 3620, 3480, 2940, 2875, and 1100 cm$^{-1}$; nmr (CDCl$_3$) δ 3.80–4.00 (8H, m, —OCH$_2$CH$_2$O—), 3.40–3.75 (2H, br. m, —CH$_2$O—), 1.00 (3H, S, C-19 —CH$_3$), 0.66 (3H, S, C-18 —CH$_3$); mass spectrum (m/e) 462 (M+), 390, 265.

Anal. Calc'd for C$_{23}$H$_{46}$O$_2$: C, 72.69; H, 10.02; O, 17.29. FOUND: C, 72.50; H, 9.87; O, 17.04.

EXAMPLE 4

Preparation of 3,6-dioxo-24-p-toluenesulfonoxy-5α-cholane diethylene ketal (Compound D)

To a solution of 15.00 g (0.0324 mole) of alcohol C in 70 ml of anhydrous pyridine was added 7.76 g (0.041 mole) of p-toluenesulfonyl chloride at room temperature. The reaction mixture was cooled at 3° C. for 67 hours and then poured into 1 l of ice and water with stirring and cooling. After an additional 1.5 hours of stirring the milky solution was extracted with 2 l of diethyl ether. The ether solution was dried (Na$_2$SO$_4$), filtered through activated charcoal, washed with 300 ml of 5% aqueous hydrochloric acid, 300 ml of water, dried again (Na$_2$SO$_4$) and concentrated under reduced pressure to afford 13.80 g (69%) of the crude tosylate as an oil. Upon prolonged drying under vacuum this oil became a white solid, m.p. 45°–55° C. A small amount of this sample was dissolved in acetone and treated with water. An oil formed. The solvents were decanted from the oil and the residue upon drying became a white solid, C, m.p. 63°–68° C.; ir (CHCl$_3$) 2940, 2880, 1600, 1360, 1190, 1175, and 1100 cm$^{-1}$; nmr (CDCl$_3$) δ 7.20–7.90 (4H, m, aromatic), 3.75–4.10 (8H, m, —OCH$_2$CH$_2$O—), 2.45 (3H, S, Ar—CH$_3$), 1.01 (3H, S, C-19 —CH$_3$), 0.64 (3H, S, C-18 —CH$_3$). This material did not give satisfactory combustion analysis.

EXAMPLE 5

Preparation of 3,6-dioxo-25-cyano-5α-cholane diethylene ketal (Compound E)

A. From tosylate 5. A solution of 2.00 g (0.003 mole) of tosylate D and 1.3 g (0.019 mole) of potassium cyanide in 72 ml of dimethyl formamide was heated with stirring at 98° C. for 23 hours. The cooled reaction mixture was then poured into 100 ml of ice water. After stirring for an additional hour the solid was collected by filtration and washed on the filter with 2×25 ml of water to afford 1.31 g (86%) of the cyano derivative E as a pale beige powder, m.;. 60°–65° C.

B. From alcohol C without purification of the tosylate intermediate. To a solution of 2.00 g (0.004 mole) of alcohol C and 10 ml of anhydrous pyridine was added 1.00 g (0.005 mole) of p-toluenesulfonyl chloride at room temperature. The reaction mixture was cooled at 3° C. for 21.5 hours and then poured into 250 ml of 5% aqueous hydrochloric acid with cooling and stirring. This solution was heated to 50° C. and the liquid decanted from an oily residue. This oil solidified when stirred for a few minutes with water. This solid was pulverized and washed with cold water to afford the tosylate D as a white powder, m.p. 51°–56° C. A solution of this white powder and 1.70 g (0.026 mole) of potassium cyanide in 80 ml of dimethyl formamide was heated at 90° C. for 22 hours, cooled to 25° C., poured into 300 ml of cold water, and filtered to afford 1.686 g (87%) of the cyanide E as an off-white powder, m.p. 62°–68° C.; ir (CHCl$_3$) 2960, 2890, 2260, 1460, 1390, 1370, 1215, and 1105 cm$^{-1}$; nmr (CDCl$_3$) δ 3.83–4.02 (8H, m, —OCH$_2$CH$_2$O), 2.30–2.50 (2H, br. m, —CH$_2$CN), 1.05 (3H, S, C-19 —CH$_3$), 0.68 (3H, S, C-18 —CH$_3$); mass spectrum (m/e) 399 (M+ −72), 274.

Anal. Calc'd for $C_{29}H_{45}NO_4$: C, 73.84; H, 9.62; N, 2.97; O, 13.57. FOUND: C, 73.22; H, 9.68; N, 2.73; O, 13.33.

EXAMPLE 6

Preparation of 3,6-dioxo-24-carboxy-5α-cholane diethylene ketal (Compound F)

A solution of 17.10 g (0.036 mole) of cyanide E in 257 ml of ethanol and 257 ml of 10 N aqueous sodium hydroxide was heated at reflux for 48 hours. The bulk of the ethanol was removed under reduced pressure and to the residue was added 2.6 l of water and 220 ml of concentrated hydrochloric acid. After 0.5 hour of stirring and cooling, the solid was collected by filtration, and washed on the filter with 2×700 ml of cold water to afford 17.60 g (99%) of the acid F as an off-white powder, m.p. 86°-99° C.; ir (CHCl$_3$) 3600-2500 (broad), 2950, 2890, 1710 and 1110 cm$^{-1}$; nmr (CDCl$_3$) δ 6.40-6.55 (1H, br. m, COOH), 3.80-4.02 (8H, m, —OCH$_2$CH$_2$O—), 1.02 (3H, S, C-19 —CH$_3$), 0.67 (3H, S, C-18 —CH$_3$); mass spectrum (m/e) 490 (M+), 475, 418, 293.

Anal. Calc'd for $C_{29}H_{46}O_6$: C, 70.99; H, 9.45; O, 19.56. FOUND: C, 70.62; H, 9.29; O, 19.61.

EXAMPLE 7

Preparation of 3,6-dioxo-25-carbomethoxy-5α-cholane diethylene ketal (Compound G)

To a solution of 10.80 g (0.022 mole) of acid F in 65 ml of hexamethylphosphorictriamide was added a solution of 1.32 g (0.033 mole) of sodium hydroxide in 4 ml of water at room temperature. This solution was stirred for 1 hour at room temperature at which time 12.50 g (0.088 mole) of methyl iodide was added dropwise over a period of 30 minutes. The reaction mixture was allowed to stir for 24 hours at room temperature and then poured into 110 ml of 5% aqueous hydrochloric acid. This solution was extracted with 1.1 l of diethyl ether and the ether extract was washed with 220 ml of water, dried (Na$_2$SO$_4$), filtered through activated charcoal and concentrated under reduced pressure to afford 13.114 g of a yellow oil. A solution of 11.836 g of this material in 200 ml of diethyl ether was stirred briefly with basic alumina, filtered, washed with 20 ml of water, dried (Na$_2$SO$_4$), filtered through activated charcoal, and concentrated to yield 9.695 g (97%) of the ester G as a viscous pale yellow liquid. This liquid turned to a very hard and tacky solid upon prolonged vacuum drying. ir (CHCl$_3$) 2950, 2880, 1730, and 1100 cm$^{-1}$; nmr (CDCl$_3$) δ 3.75-4.00 (8H, m, —OCH$_2$CH$_2$O—), 0.97 (3H, S, C-19—CH$_3$), 0.62 (3H, S, C-18—CH$_3$), mass spectrum (m/e) 504 (M+) 432, 307.

This sample did not give satisfactory combustion analysis but was suitable for further reaction.

EXAMPLE 8

Preparation of 25-hydroxycholestane-3,6-dione diethylene ketal (Compound H)

To a solution of 54 ml (0.156 mole) of ethereal methylmagnesium bromide in 190 ml of dry tetrahydrofuran in a predried 500 ml 3-necked flask fitted with stirrer, reflux condenser, and dropping funnel was added dropwise a solution of 8.727 g (0.0173 mole) of ester G in 60 ml of tetrahydrofuran over a period of 30 minutes at room temperature under argon. The reaction mixture was stirred at room temperature for 24 hours at which time it was added via a dropping funnel to a solution of 33.4 g of ammonium chloride in 244 ml of water dropwise with cooling over a period of 30 minutes. After stirring for an additional 30 minutes, the bulk of the tetrahydrofuran was removed under reduced pressure. The aqueous residue was extracted with 425 ml of chloroform and the chloroform extract was washed with 100 ml of water, dried (Na$_2$SO$_4$), filtered through activated charcoal, and concentrated to afford 9.07 g (100%) of H as an off-white solid, m.p. 52°-57° C. A small amount of this material was dissolved in boiling methanol and water added to the cloudy point. Upon cooling a yellow oil separated. The mother liquid was decanted and the oil dried under vacuum to afford a white solid, m.p. 66°-71° C.; ir (CHCl$_3$) 3610, 3470, 2950, 2880, and 1100 cm$^{-1}$; nmr (CHCl$_3$) δ 3.75-4.00 (8H, m, —OCH$_2$CH$_2$O—), 1.18 (8H, S, C-26 and C-27 —CH$_3$) 1.02 (3H, S, C-19—CH$_3$), 0.65 (3H, S, C-18 CH$_3$); mass spectrum (m/3) 504 (M+), 489, 437, 307.

Anal. Calc'd for $C_{31}H_{52}O_5$: C, 73.77; H, 10.38; O, 15.85. FOUND: C, 73.10; H, 10.15; O, 15.96.

EXAMPLE 9

Preparation of 25-hydroxycholestane-3,6-dione (Compound I)

A solution of 7.485 g (0.0148 mole) of alcohol H in 130 ml of ethanol containing 6 ml of water and 6 ml of concentrated sulfuric acid was heated at reflux for 1.25 hours. The reaction mixture was cooled and poured into 1.4 l of ice water. The product was collected by filtration and washed on the filter with 2×750 ml of water to afford 4.635 g (75%) of an off-white powder, m.p. 146°-156° C. Pour recrystallation of this material from n-heptane gave an analytical sample of I as a white crystalline solid, m.p. 187°-191° C. (literature[5] value 184°-188° C.); ir (CHCl$_3$) 3515, 3450, 2950, 2875, and 1710 cm$^{-1}$; nmr (CDCl$_3$) δ 1.22 (6H, S, C-26 and C-27 —CH$_3$), 0.97 (3H, S, C-19 —CH$_3$), 0.72 (3H, S, C-18 —CH$_3$); mass spectrum (m/e) 401 (M+ — 15), 398.

Anal. Calc'd for $C_{27}H_{44}O_3$: C, 77.84; H, 10.64; O, 11.52. FOUND: C, 77.79; H, 10.75; O, 11.34.

While only certain embodiments and certain variations of my invention have been described, it will be apparent to those skilled in this art that other embodiments may be practiced and that many changes may be made, all within the spirit of the invention and included within the scope of the appended claims.

What is claimed:

1. In a process for preparing a 3,6-diketo steroid compounds, the step of heating a compound having the structure:

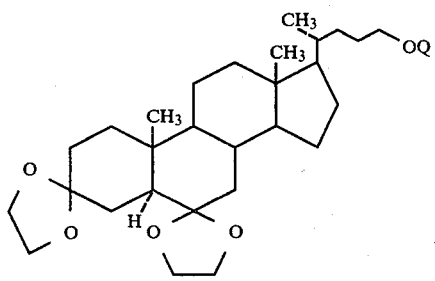

with a metal cyanide, where Q is an aryl or alkyl sulfonyl group to produce the compound having the structure:

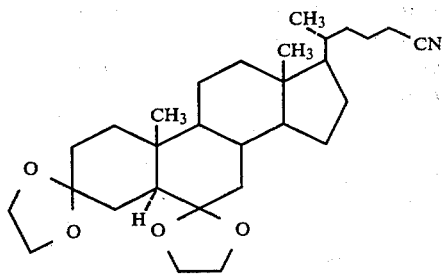

2. A process as set forth in claim 1 in which said sulfonyl group is p-toluenesulfonyl.

3. A process as set forth in claim 1 in which said metal cyanide is potassium cyanide.

4. A process as set forth in claim 1 in which said metal cyanide is sodium, lithium, or silver cyanide.

5. A process as set forth in claim 1 including the set of mixing a compound having the structure:

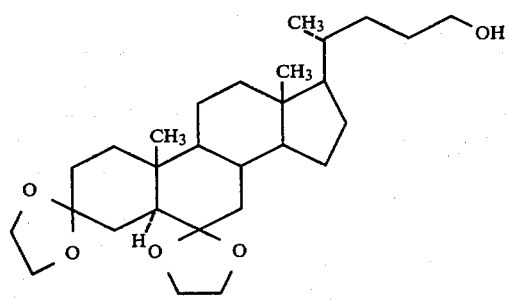

with an aryl or alkyl sulfonyl halide to replace OH with a sulfonyl ester group to prepare said compound having the structure:

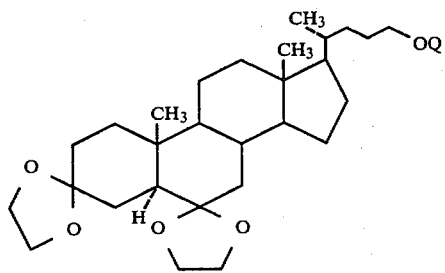

where Q is an alkyl or aryl sulfonyl group.

6. A process as set forth in claim 5 in which said aryl sulfonyl halide is p-toluenesulfonyl halide.

7. A process as set forth in claim 5 including the step of mixing a compound having the structure:

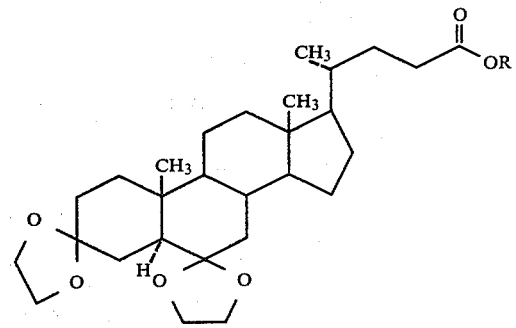

where R is a lower alkyl group, with an alkaline reducing agent to reduce the 24-carboxylic ester function to a 24-hydroxy group.

8. A process as set forth in claim 7 in which said reducing agent is a complex of aluminum hydride with sodium, potassium or lithium.

9. A process as set forth in claim 7 including the step of heating a compound having the structure:

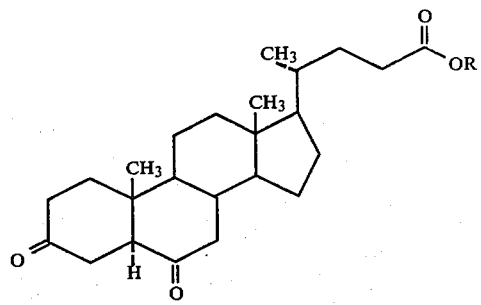

where R is a lower alkyl group with ethylene glycol and a sulfonic acid catalyst to prepare said compound having the structure:

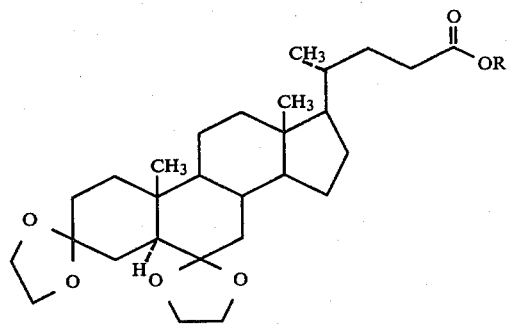

10. A process as set forth in claim 9 in which said sulfonic acid is p-toluenesulfonic acid.

11. A process as set forth in claim 1 including the step of refluxing in an aqueous alcohol solution of said compound having the structure:

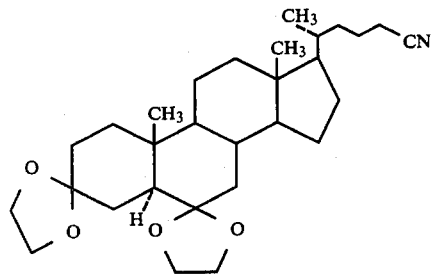

with sodium or potassium hydroxide and acidifying the resulting compound to prepare a compound having the structure:

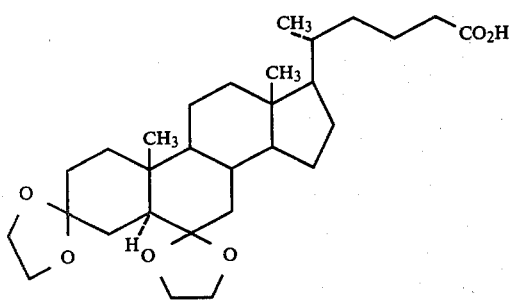

12. A process as set forth in claim 11 including the step of mixing in the presence of sodium or potassium hydroxide a solution of said compound having the structure:

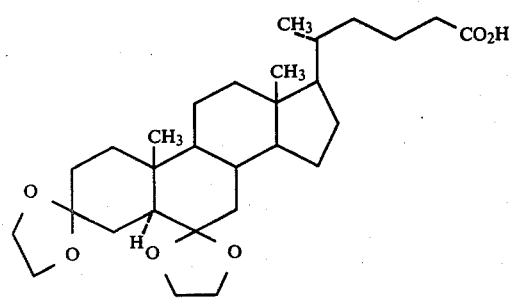

with an alkyl halide to prepare a compound having the structure:

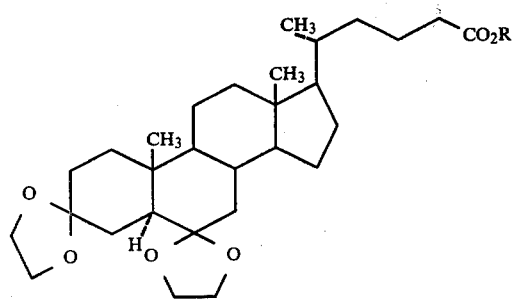

where R is alkyl.

13. A process as set forth in claim 12 where said alkyl halide is methyl iodide.

14. A process as set forth in claim 12 including the step of mixing a solution of a methyl magnesium halide, dissolved in an ether, with said compound having the structure:

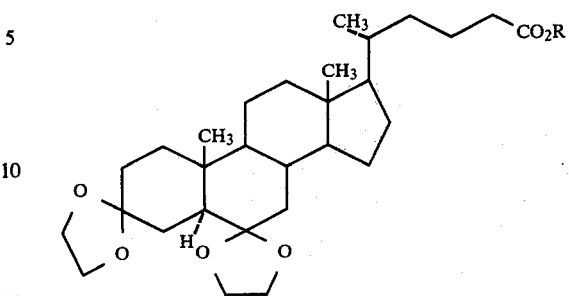

where R is alkyl to prepare a compound having the structure:

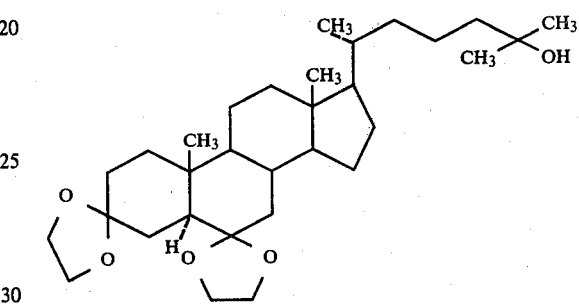

15. A process as set forth in claim 14 where said metallo-methyl complex is methyl magnesium bromide.

16. A process as set forth in claim 14 in which said ether solvent is tetrahydrofuran.

17. A process as set forth in claim 14 including the step of heating an aqueous acid-containing alcohol solution of said compound having the structure:

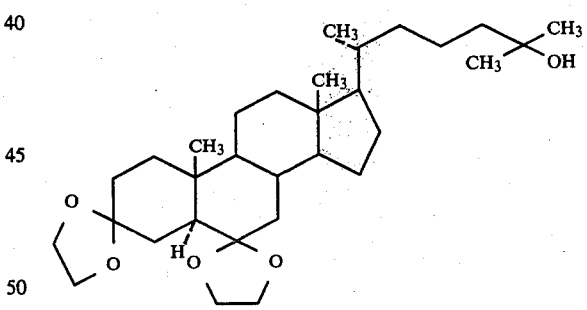

to prepare a compound having the structure:

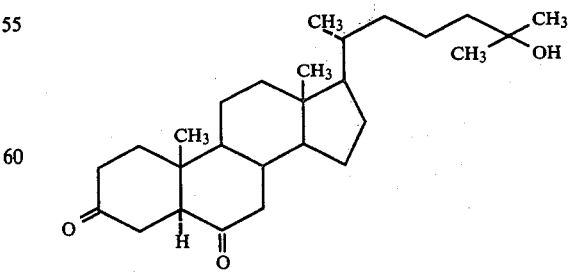

18. A process as set forth in claim 17 where the aqueous acid is sulfuric acid diluted with water.

* * * * *